(12) United States Patent
Typpoe et al.

(10) Patent No.: US 7,146,279 B2
(45) Date of Patent: Dec. 5, 2006

(54) MEASURING DEVICE

(75) Inventors: Pekka Typpoe, Cupertino, CA (US); Rudolf Muench, Koenigsbronn (DE); Thomas Ischodonat, Bachhagel (DE)

(73) Assignee: Voith Paper Patent GmbH, Heindenheim (DE)

( * ) Notice: Subject to any disclaimer, the term of this patent is extended or adjusted under 35 U.S.C. 154(b) by 0 days.

(21) Appl. No.: 11/017,122

(22) Filed: Dec. 20, 2004

(65) Prior Publication Data

US 2005/0150288 A1   Jul. 14, 2005

(30) Foreign Application Priority Data

Dec. 22, 2003   (DE) ................................ 103 61 160

(51) Int. Cl.
*G01N 31/00* (2006.01)
*G01N 21/84* (2006.01)
*G01B 5/02* (2006.01)

(52) U.S. Cl. ............................ 702/22; 702/27; 702/28; 702/170; 702/172; 356/429

(58) Field of Classification Search ................. 702/22, 702/23, 27, 28, 155, 158, 170, 172; 356/429, 356/630; 73/159
See application file for complete search history.

(56) References Cited

U.S. PATENT DOCUMENTS

| 4,282,998 A | 8/1981 | Peekna ........................ 226/97 |
| 5,209,103 A | 5/1993 | Driviere et al. ................. 73/37 |
| 5,233,195 A | 8/1993 | Hellstrom et al. ........ 250/360.1 |
| 5,770,949 A | 6/1998 | Sgro ........................... 324/229 |
| 5,826,627 A | 10/1998 | Seabrook et al. ....... 139/383 A |
| 6,421,415 B1* | 7/2002 | Peczkis et al. ................. 378/46 |
| 6,494,081 B1 | 12/2002 | Moisio ........................ 73/37.7 |
| 6,588,118 B1 | 7/2003 | Hellstrom ................. 33/501.02 |
| 6,743,338 B1* | 6/2004 | Graeffe et al. ............... 162/198 |
| 2003/0024301 A1 | 2/2003 | Graeffe et al. ............... 73/37.6 |
| 2003/0066200 A1* | 4/2003 | Hellstrom ................. 33/501.02 |

FOREIGN PATENT DOCUMENTS

| DE | 2342926 | 9/1972 |
| DE | 19620389 | 4/1997 |

* cited by examiner

*Primary Examiner*—Bryan Bui
*Assistant Examiner*—Meagan S Walling
(74) *Attorney, Agent, or Firm*—Taylor & Aust, P.C.

(57) ABSTRACT

A device for measuring at least one property of a material web, in particular a paper or board web, includes movable measuring probes provided on both sides of the web, which can be pressed against the web with preferably at least substantially equal force, forming a respective air pad, elements for measuring the air pads, in particular the air pad thickness, on both sides, and at least one property sensor, in particular a paper property sensor, fitted to a measuring probe supported by an air pad.

33 Claims, 4 Drawing Sheets

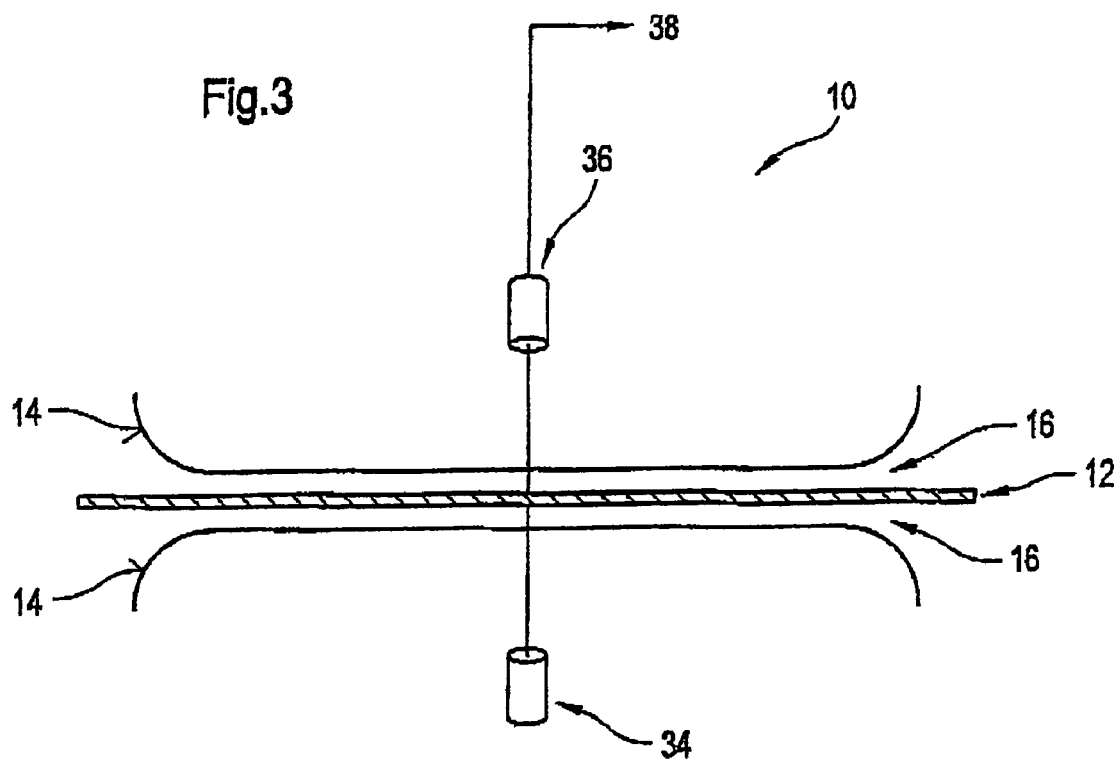
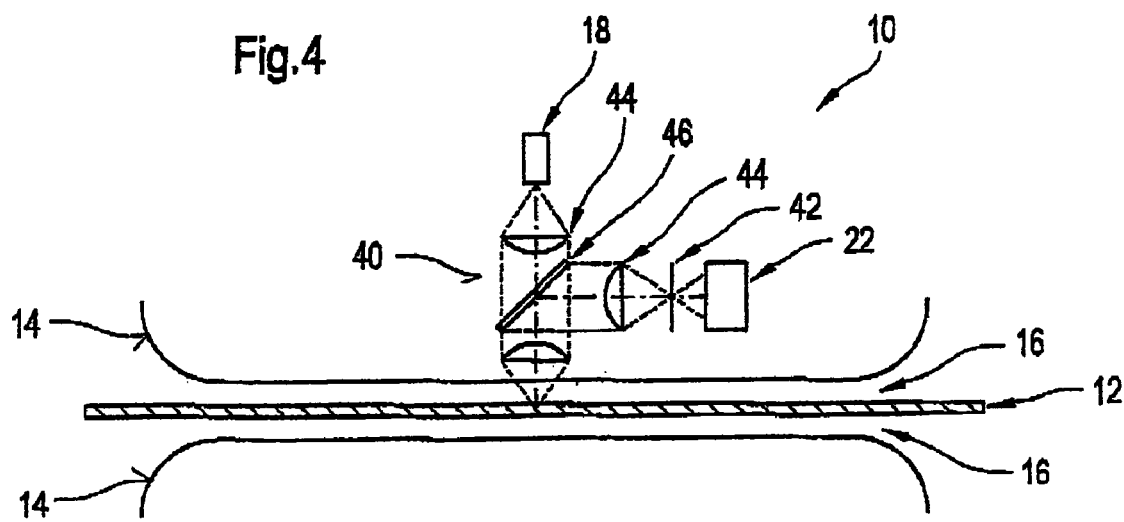

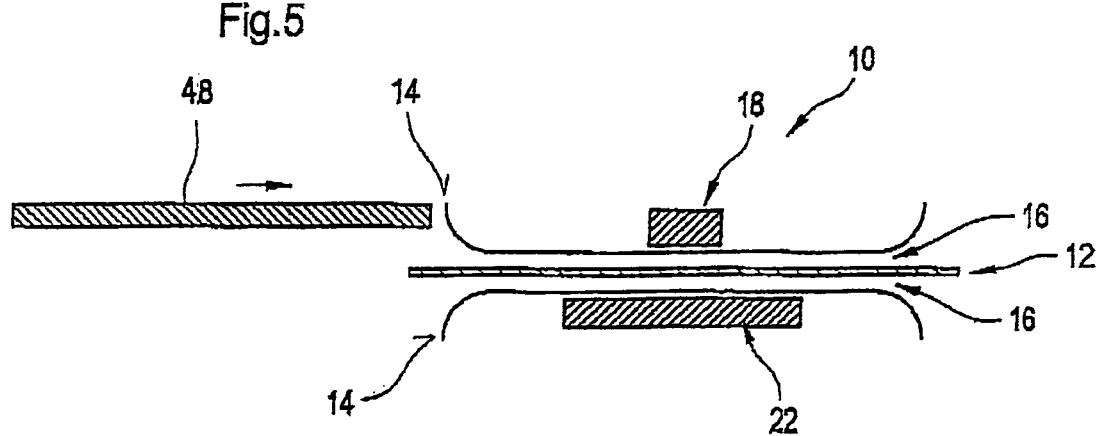
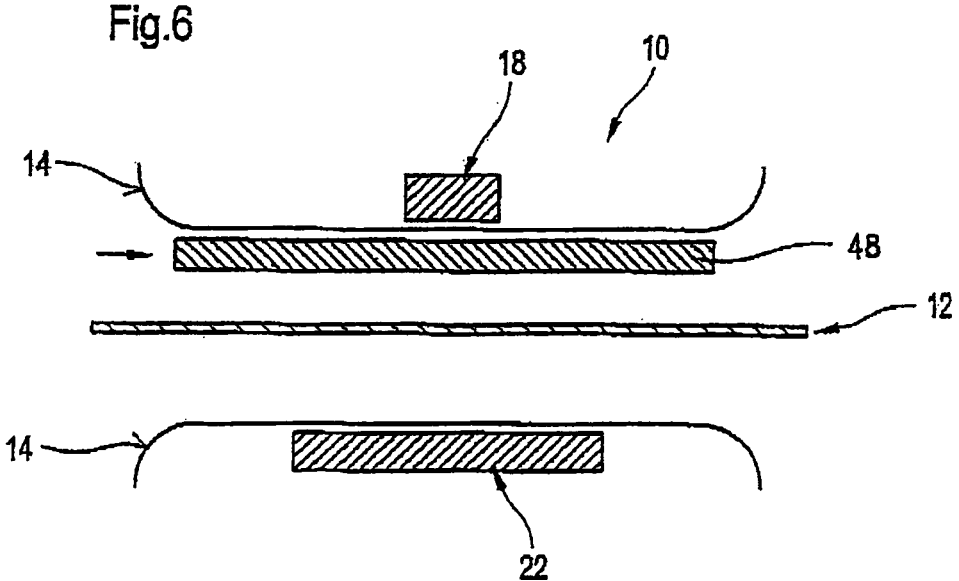

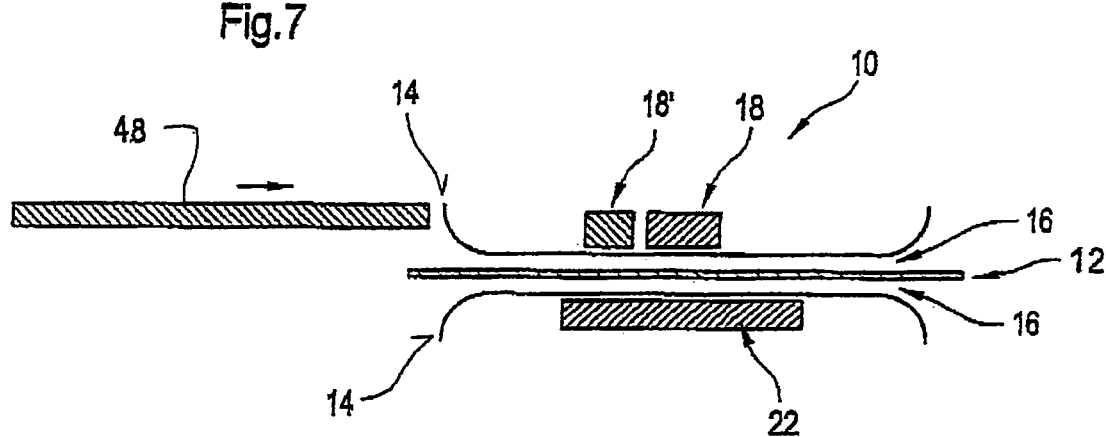
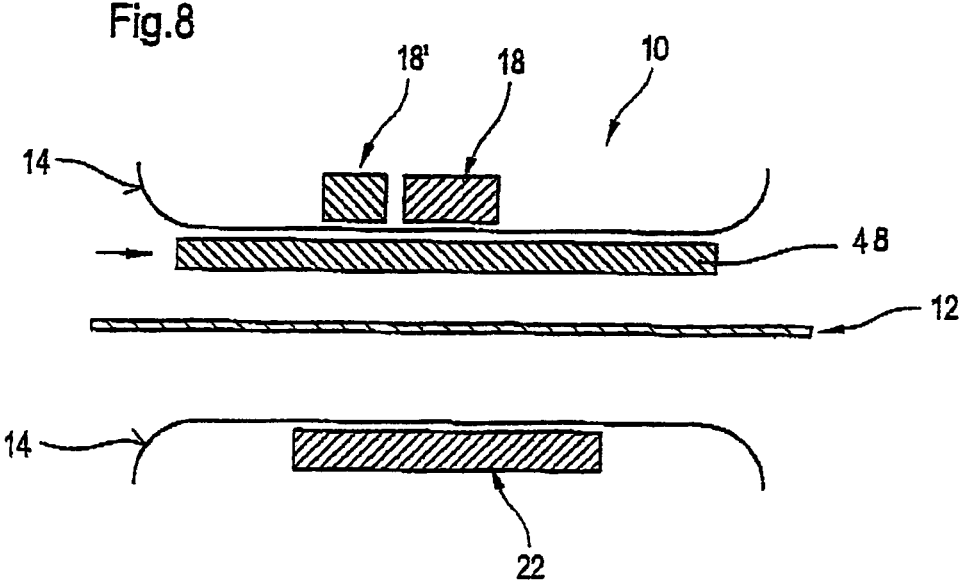

MEASURING DEVICE

BACKGROUND OF THE INVENTION

1. Field of the Invention

The present invention relates to a measuring device for measuring at least one property of a material web, in particular a paper and/or board web.

2. Description of the Related Art

Various paper quality sensors are known, in which the measurement is normally carried out over a measuring gap whose thickness is several millimeters. Examples which may be mentioned of sensors which are relevant to the present invention are:

- gloss sensor,
- formation sensor,
- surface roughness sensor,
- grammage and ash sensors (sensors with radioactive sources),
- ash sensors for measuring a respective composition by way of x-ray fluorescence,
- grammage sensor based on an x-ray tube for measuring the total ash content and the ash composition.

Most of the sensors mentioned above can certainly currently be obtained as such. However, they require an extremely stable and therefore costly scanning mechanism in order to maintain the alignment of the sensors when the latter are moved over the sheet. What is needed in the art is a device where the requirements on accuracy for the scanning mechanism are reduced considerably.

SUMMARY OF THE INVENTION

The present invention provides a family of sensors provided with air pads with which the problems connected with the measuring gap variations are eliminated. Most sensors are sensitive with respect to such variations in the gap thickness. A stable air pad can eliminate the errors produced by gap thickness variations, while contact with the paper sheet or paper web continues to be prevented. In this case, all the critical components are fitted to measuring probes which ride on the sheet or the web, being separated from the sheet or web by an air pad, of which the thickness is kept constant and which has a thickness which corresponds to only a fraction of a millimeter (normally 0.1 to 0.2 mm on each sheet side).

All gloss sensors require highly accurate alignment with respect to the sheet, so that the arrangement having a stable air pad provides an ideal platform for a gloss sensor. The same applies to an optical formation sensor for measuring and analyzing the extremely fast variations with respect to the optical transmission through the sheet.

Measuring the surface roughness can be carried out within the air pad or measuring gap either by way of an optical measurement of the surface topography at high speed, or by way of measuring the air pad thickness, the air flow into the air pad, the web speed and the activating force. This data gives the flow resistance, which correlates with the surface roughness.

The grammage measurement can be carried out within the air pad of the measuring gap by the detector being arranged or mounted on one side of the sheet and the radioactive beta source on the other side of the sheet. The radioactive source requires a shutter mechanism which, for example, can be a sliding shutter which moves with the source when the measuring probe is drawn back over the air pad surface, or can be a mechanism with which the source capsule can be moved away from the air pad arrangement into a shielded position. The advantage of this arrangement is that both the geometric sensitivity with respect to the measuring gap variation and the errors which are produced by the variable air mass in the gap are eliminated. A further advantage results from the fact that, with the provision of the source and the detector, the efficiency with respect to radiation capture, which denotes either that smaller or virtually all the radiation passing through the sheet reaches the detector, which is associated with a very low sensitivity to ash. In addition, the sensitivity with respect to fluttering is eliminated.

By using this procedure, even the measurement of kaolin constituents by using x-ray fluorescence is made easier, as long as the kaolin is distributed uniformly in the sheet. When using a conventional sensor, the low fluorescence energies emitted by the kaolin are absorbed in the air without reaching the detector. By using a thin and regulated air pad, however, the absorption in air is reduced to a minimum, which makes the measurement possible.

If all the significant ash components can be measured either by way of x-ray fluorescence or by way of monitoring the absorption of x-rays at various energy levels in such a way that the ash components can be determined independently of the total absorption, then it becomes possible to measure the grammage of the sheet with x-rays. An x-ray sensor (for example one based on an Fe-55 tube) can then be used for the purpose of measuring the grammage, the ash content and the ash composition. The key is formed by the possibility of measuring kaolins. $TiO_2$ and $CaCO_3$ can be measured even with larger measuring gaps.

According to one aspect, the present invention provides in particular a device for measuring at least one property of a material web, in particular a paper or board web, having movable measuring probes provided on both sides of the web, which can be pressed against the web with preferably at least substantially equal force, forming a respective air pad, having elements for measuring the air pad, in particular the air pad thickness, on both sides of the web, and having at least one property sensor, in particular a paper property sensor, arranged on or fitted to a measuring probe supported by an air pad.

A further aspect of the present invention provides a device for measuring the paper roughness, having movable measuring probes provided on both sides of the paper web, which can be pressed against the web with preferably at least substantially equal force, forming a respective air pad, stable air pads on both sides of the web, elements for measuring the air pad thickness, elements for measuring the flow into the air pad, elements for measuring the air temperature in order to determine the viscosity of air, force elements for compressing the air pad against the material web, elements for calculating the flow resistance on the basis of the air pad thickness, the flow, the temperature and the force, and elements for calculating the surface roughness on the basis of the flow resistance.

According to a further aspect, the present invention provides a device for measuring at least one paper property, having movable measuring probes provided on both sides of the paper web, which can be pressed against the web with at least substantially equal force, forming a respective air pad, stable air pads on both sides of the web, a radiation source on one side of the web and a radiation detector on the other side of the web for measuring paper properties.

Preferred embodiments of the measuring device according to the present invention are specified in the dependent claims.

Using the present invention, a considerably higher accuracy is achieved and a substantially more economical scanning frame for various different measurements is made possible, in which the sensors or measuring probes are arranged on a stable air pad, by which elements errors which are produced by gap thickness variation, sheet flutter and air density variations are eliminated.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 3 is a schematic view of an embodiment of the measuring device in which the optical paper quality sensor provided is a formation sensor according to the present invention;

FIG. 4 is a schematic view of an embodiment of measuring device in which the optical paper property sensor provided is a surface roughness sensor according to the present invention;

FIG. 5 is a schematic view of an embodiment of the measuring device having a radiation sensor as a paper property sensor in a phase in which the beam is let through with the shutter open according to the present invention;

FIG. 6 is a schematic view of the radiation sensor according to FIG. 5 with the shutter closed;

FIG. 7 is a schematic view of a measuring device having a nuclear sensor with x-ray fluorescence as paper property sensor in a phase in which the shutter is opened according to the present invention; and FIG. 8 is a schematic view of the nuclear sensor according to FIG. 7 with the shutter closed.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
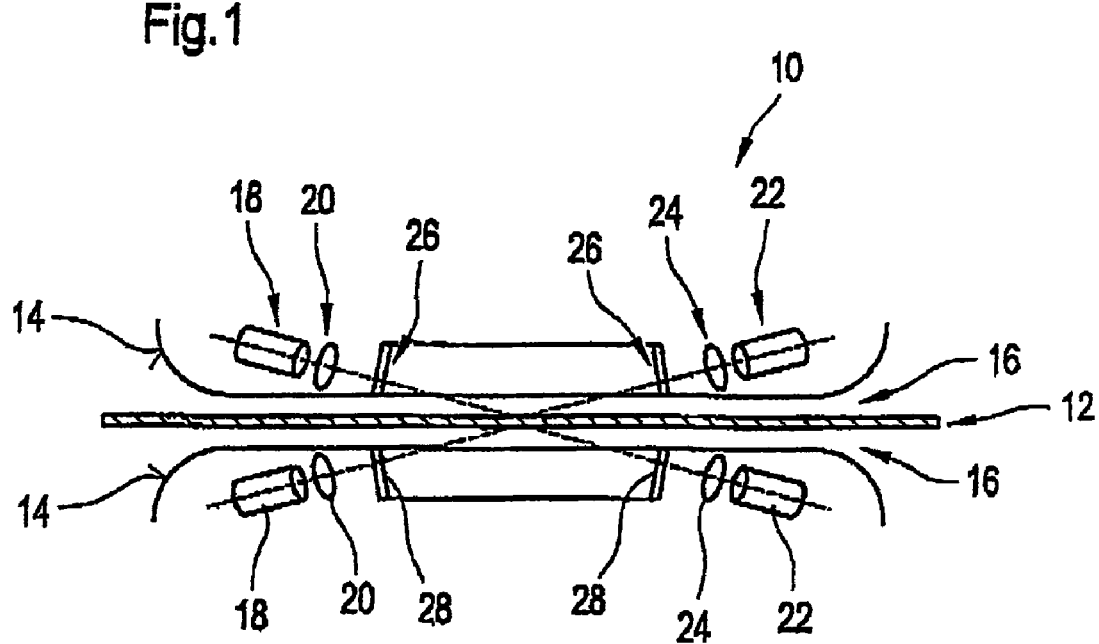
FIG. 1 is a schematic view of an embodiment of the measuring device with a gloss sensor provided on both sides of the material web according to the present invention.

Referring now to the drawings, and more particularly to FIG. 1, there is shown a measuring device 10 having a gloss sensor provided on both sides of the sheet or material or fiber web 12, in particular a paper or board web.

Measuring device 10, arranged in the present case for example for measuring the gloss, includes movable measuring probes 14 which are provided on both sides of the web and which can be pressed against material web 12, forming a respective stable air pad 16. In this case, measuring probes 14 can be pressed against web 12 with equal or with different force. Elements are provided for measuring the air pad, in particular the air pad thickness, on both sides of the web. At least one paper property sensor arranged on or fitted to a measuring probe 14 supported on an air pad 16 is provided.

As already mentioned, the paper property sensor in the present case is a gloss sensor arranged on both sides of material web 12.

The light source of the gloss sensor in the present case includes two white LED's (light emitting diodes) 18 on the two sides of material web 12. In each case a lens 20 is arranged after these two white LED's 18. Moreover, in each case a detector 22 with a lens 24 in front is provided on the two sides of material web 12.

As can be seen from FIG. 1, the light beam coming from the respective light source or LED 18 passes directly through source window 26 and receiving window 28 to the relevant detector 22 on the other side of the web.

The present gloss sensor is therefore an optical paper property sensor.

Figure 2:
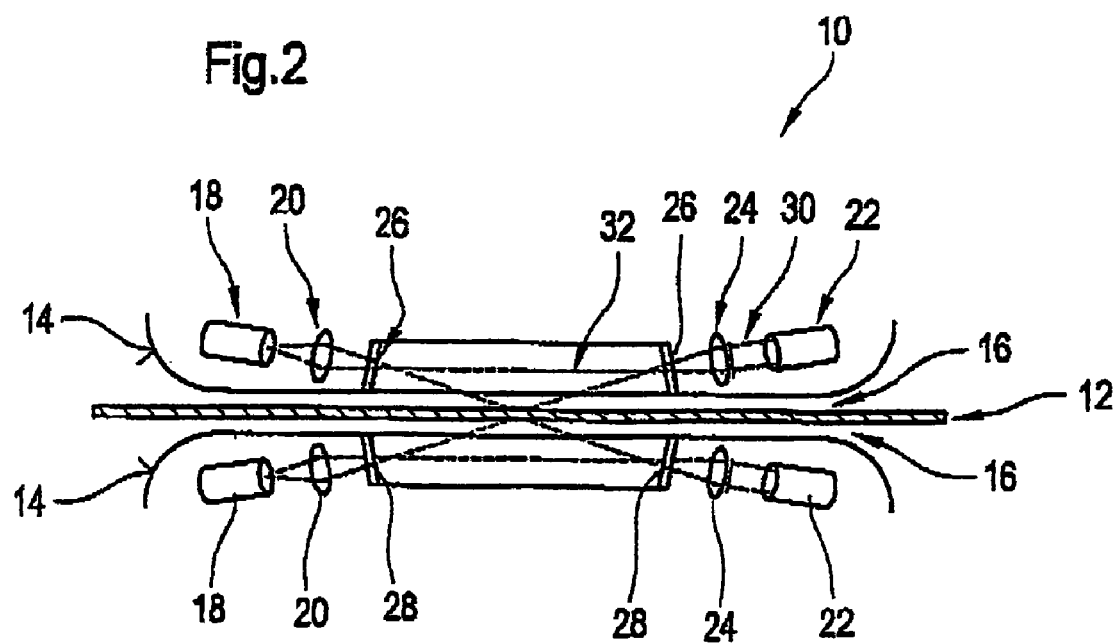
FIG. 2 is a schematic view of an embodiment of the measuring device with a gloss sensor with reference beam provided on both sides of the material web according to the present invention.

FIG. 2 shows, in a schematic illustration, an embodiment of the measuring device 10 having a gloss sensor with reference beam arranged on both sides of material web 12. The present embodiment therefore differs from that of FIG. 1 essentially in the fact that the beam coming from the light source or white LED 18 is divided into a measuring beam 30 and a reference beam 32, which passes directly through source window 26 and receiving window 28 to a separate reference detector 22. Detectors 22 are therefore in each case what are known as a dual detector.

Otherwise, the arrangement according to FIG. 2 can again have at least substantially the same structure as that of FIG. 1. Mutually corresponding parts are assigned the same designations.

FIG. 3 shows, in a schematic illustration, an embodiment of the measuring device 10 in which the optical paper property sensor provided is a formation sensor. As can be seen from FIG. 3, in the present case, too, in each case a stable air pad 16 is again provided between measuring probes 14 arranged on the two sides of material web 12. The lower measuring probe 14 is assigned a laser 34, and the upper measuring probe 14 is assigned a detector 36, whose output signal can be supplied to a signal processor 38 or the like, for example.

FIG. 4 shows, in a schematic illustration, an embodiment of measuring device 10 in which the optical paper property sensor provided is a surface roughness sensor.

In the present case, too, in each case an air pad 16 is again provided between the measuring probes 14 arranged on the two sides of the web and material web 12. Measuring device 10 or the surface roughness sensor can, for example, be provided with a laser or an LED source and lens optics 40, in order to measure the surface topography on the basis of the measurement of the size of the focal spot on the web surface. In this case, as illustrated in FIG. 4, a precision aperture plate 42 with a pinhole can be arranged in front of detector 22, which has the effect that the signal supplied by detector 22 decreases when the web surface moves away from the ideal focal point.

As can be seen from FIG. 4, lens optics 40 include a beam splitter 46 in addition to lenses 44 and precision aperture plate 42. Light from source 18 passes through this beam splitter 46 to material web 12. In addition, the light reflected from material web 12 is deflected toward detector 22 by this beam splitter 46.

FIGS. 5 and 6 also in each case again show a measuring device 10 having movable measuring probes 14 provided on both sides of the paper web, which can be pressed against the web with substantially equal or different force, forming a respective air pad 16, stable air pads 16 on both sides of the web, a radiation source 18 on one side of the web and a radiation detector 22 on the other side of the web for measuring one or more paper properties. In the present case, radiation source 18 provided is a radioactive source and detector 22 provided is an appropriate radiation detector.

FIG. 5 shows the relevant measuring device 10 or the relevant radiation sensor in a phase in which the beam is let through with shutter 48 open. FIG. 6 shows the radiation sensor according to FIG. 5 with shutter 48 closed.

As can be seen from FIGS. 5 and 6, the beam can be interrupted by way of shutter 48, by the latter being pushed over radiation source 18 when measuring probe 14 is drawn back from material web 12.

FIGS. 7 and 8 show an embodiment of measuring device 10 having a nuclear sensor with x-ray fluorescence. In the present case, source 18 is therefore, for example, a radioactive source or x-ray tube, and detector 22 on the opposite side of the web is an appropriate radiation detector. In addition, an x-ray fluorescence detector 18' is provided on the same side of the web as source 18.

FIG. 7 shows the nuclear sensor with x-ray fluorescence in a phase in which shutter 48 is open, that is to say the radiation can pass through material web 12.

In FIG. 8, on the other hand, the nuclear sensor is again shown in a phase in which shutter 48 is closed.

As can be seen from FIGS. 7 and 8, in the present case shutter 48 can again be pushed over source 18 when measuring probe 14 is drawn back from material web 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF DESIGNATIONS

10 Measuring device
12 Sheet, material web
14 Measuring probe
16 Air pad
18 White LED, light source, radioactive source or x-ray tube
18' X-ray fluorescence detector
20 Lens
22 Detector, reference detector
24 Lens
26 Source window
28 Receiving window
30 Measuring beam
32 Reference beam
34 Laser
36 Detector
38 Signal processor
40 Lens optics
42 Aperture plate
44 Lens
46 Beam splitter
48 Shutter

What is claimed is:

1. A device for measuring at least one property of a fiber web, comprising:
   a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web, each of said plurality of movable measuring probes being pressed against the fiber web with an at least substantially equal force;
   at least one element for measuring said at least one respective air pad on said each side of the fiber web; and
   at least one property sensor being one of arranged on at least one of said movable measuring probes supported by at least one said respective air pad and fitted to at least one of said movable measuring probes supported by at least one said respective air pad.

2. The device of claim 1, wherein said fiber web is one of a paper web and a board web.

3. The device of claim 1, wherein said at least one element for measuring said at least one air pad measures an air pad thickness.

4. The device of claim 1, wherein said at least one property sensor is a paper property sensor.

5. The device of claim 1, further including at least one optical property sensor.

6. The device of claim 5, wherein said at least one optical property sensor measures a surface roughness of the fiber web.

7. The device of claim 1, further including at least one optical gloss sensor.

8. A device for measuring at least one property of a fiber web, comprising:
   a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
   at least one element for measuring said at least one respective air pad on said each side of the fiber web;
   at least one property sensor being one of arranged on at least one of said movable measuring probes supported by at least one said respective air pad and fitted to at least one of said movable measuring probes supported by at least one said respective air pad; and
   at least one optical gloss sensor arranged on each side of the fiber web.

9. A device for measuring at least one property of a fiber web, comprising:
   a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
   at least one element for measuring said at least one respective air pad on said each side of the fiber web;
   at least one property sensor being one of arranged on at least one of said movable measuring probes supported by at least one said respective air pad and fitted to at least one of said movable measuring probes supported by at least one said respective air pad;
   at least one optical gloss sensor; and
   a light source providing a light beam being divided into a measuring beam and a reference beam, said reference beam passing directly through a source window and a receiving window to a separate reference detector.

10. The device of claim 9, wherein at least one said optical gloss sensor is arranged on each said side of the fiber web.

11. A device for measuring at least one property of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
at least one element for measuring said at least one respective air pad on said each side of the fiber web;
at least one property sensor being one of arranged on at least one of said movable measuring probes supported by at least one said respective air pad and fitted to at least one of said movable measuring probes supported by at least one said respective air pad;
at least one optical gloss sensor; and
a light source being associated with a respective said gloss sensor, said light source including a white light emitting diode.

12. A device for measuring at least one property of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
at least one element for measuring said at least one respective air pad on said each side of the fiber web;
at least one property sensor being one of arranged on at least one of said movable measuring probes supported by at least one said respective air pad and fitted to at least one of said movable measuring probes supported by at least one said respective air pad; and
at least one optical formation sensor.

13. A device for measuring at least one property of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
at least one element for measuring said at least one respective air pad on said each side of the fiber web; and
at least one property sensor being one of arranged on at least one of said movable measuring probes supported by at least one said respective air pad and fitted to at least one of said movable measuring probes supported by at least one said respective air pad; and
at least one optical property sensor, said at least one optical property sensor measuring a surface roughness of the fiber web; said at least one optical property sensor is at least one optical surface roughness sensor with both a light emitting diode source and a lens optic in order to measure a surface topography on a basis of a measure of a size of a focal spot on a surface of the fiber web.

14. The device of claim 13, wherein said at least one optical property sensor includes a detector and a precision aperture plate with a pinhole provided in front of said detector, said precision aperture plate has an effect that a signal supplied by said detector decreases when said surface moves away from an ideal focal point.

15. The device of claim 14, wherein at least one said respective air pad is a stable air pad.

16. A device for measuring a paper roughness of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side the fiber web having an air pad thickness;
at least one element for measuring said air pad thickness;
at least one element for measuring a flow into said at least one respective air pad,
at least one element for measuring an air temperature in order to determine a viscosity of air,
at least one force element for compressing said at least one respective air pad against the fiber web,
at least one element for calculating a flow resistance on a basis of said air pad thickness,
said flow, said air temperature and a force of said compressing said at least one respective air pad against the fiber web, and
at least one element for calculating the paper roughness on a basis of a flow resistance.

17. The device of claim 16, wherein each of said plurality of movable measuring probes are pressed against the fiber web with an at least substantially equal force.

18. A device for measuring at least one paper property of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;
a radiation source on one said side of the fiber web, said radiation source including a beta source for a grammage measurement; and
a radiation detector on another said side of the fiber web for measuring the at least one paper property.

19. The device of claim 18, wherein each of said plurality of movable measuring probes are pressed against the fiber web with an at least substantially equal force.

20. The device of claim 18, wherein at least one said respective air pad is a stable air pad.

21. The device of claim 18, wherein said beta source is one of a Kr-85 source and a Pm-147 source.

22. The device of claim 18, wherein said radiation source includes an x-ray source for measuring the paper ash content.

23. The device of claim 22, wherein said x-ray source is one of an Fe-55 source and a x-ray tube.

24. The device of claim 18, further including an x-ray fluorescence detector being provided to measure one of a sheet ash content composition and a web ash content composition.

25. The device of claim 24, wherein said x-ray fluorescence detector also provides for a clay measurement.

26. A device for measuring at least one paper property of a fiber web, comprising:
a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web; and a radiation detector on another said side of the fiber web for measuring the at least one paper property, said radiation source includes a radiation beam, and a shutter associated with said radiation source, said beam is interrupted by said shutter which is pushed over said radiation source when said plurality of movable measuring probes are drawn back.

27. A device for measuring at least one paper property of a fiber web, comprising:

a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web; and a radiation detector on another said side of the fiber web for measuring the at least one paper property, said radiation source includes a radiation beam, said radiation beam is interrupted by said radiation source being moved away from at least one of said plurality of movable measuring probes into a shielded position when said at least one of said plurality of movable measuring probes is drawn back from the fiber web.

28. A device for measuring at least one paper property of a fiber web, comprising:

a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web, said radiation source includes a radiation beam;

a radiation detector on another said side of the fiber web for measuring the at least one paper property; and an x-ray tube and a plurality of x-ray filters which can be inserted serially into said radiation beam in order to measure an x-ray transmission in any of a plurality of x-ray spectra and to determine at least one of an ash composition and a total ash content of one of a sheet and the fiber web.

29. The device of claim 28, further including elements for measuring a grammage by using data with respect to said ash composition together with a total x-ray absorption.

30. A device for measuring at least one paper property of a fiber web, comprising:

a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web; and a radiation detector on another said side of the fiber web for measuring the at least one paper property, at least one said respective air pad having a greater thickness than another of said at least one respective air pad.

31. The device of claim 30, wherein said thickness is a plurality of millimeters.

32. A device for measuring at least one paper property of a fiber web, comprising:

a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web; and a radiation detector on another said side of the fiber web for measuring the at least one paper property, said plurality of movable measuring probes are pressed against the fiber web with a plurality of unequal forces.

33. A device for measuring at least one paper property of a fiber web, comprising:

a plurality of movable measuring probes, at least one of said plurality of movable measuring probes being provided on each side of the fiber web, each of said plurality of movable measuring probes being pressed against the fiber web, said plurality of movable measuring probes forming at least one respective air pad on each said side of the fiber web;

a radiation source on one said side of the fiber web; and a radiation detector on another said side of the fiber web for measuring the at least one paper property, wherein a thickness of a total gap between said plurality of movable measuring probes is kept constant by way of a feedback from at least one of a plurality of compressed air measurements, a plurality of appropriate distance measurements and a plurality of thickness measurements.

* * * * *